United States Patent [19]
Corrigan, Jr. et al.

[11] Patent Number: 5,167,634
[45] Date of Patent: Dec. 1, 1992

[54] PEELABLE SHEATH WITH HUB CONNECTOR

[75] Inventors: William C. Corrigan, Jr., Randolph, N.J.; Diego Fontayne, Norwalk, Conn.

[73] Assignee: Datascope Investment Corp., Montvale, N.J.

[21] Appl. No.: 748,521

[22] Filed: Aug. 22, 1991

[51] Int. Cl.⁵ .................................... A61H 5/178
[52] U.S. Cl. .................... 604/160; 604/161; 604/164
[58] Field of Search ............ 604/160, 161, 164, 165, 604/264, 280

[56] References Cited

U.S. PATENT DOCUMENTS

| | | | |
|---|---|---|---|
| Re. 31,855 | 3/1985 | Osborne | 604/161 |
| 3,677,243 | 7/1972 | Nerz | 604/161 |
| 3,720,210 | 3/1973 | Diettrich | 604/164 |
| 3,782,381 | 1/1974 | Winnie | 604/164 |
| 4,345,606 | 8/1982 | Littleford | 128/784 |
| 4,411,654 | 10/1983 | Boarini et al. | 604/165 |
| 4,412,832 | 11/1983 | Kling et al. | 604/164 |
| 4,687,469 | 8/1987 | Osypka | 604/161 |
| 4,772,266 | 9/1988 | Groshong | 604/160 |

FOREIGN PATENT DOCUMENTS 0143517 6/1985 European Pat. Off. ............ 604/280

*Primary Examiner*—Cary E. O'Connor
*Attorney, Agent, or Firm*—Fitzpatrick, Cella, Harper & Scinto

[57] ABSTRACT

A peelable sheath includes a sheath formed of a flexible tube having a pair of separation lines arranged longitudinally on radially opposite sides of the tube to form a pair of peelable sheath portions, and a hub connector bonded to the proximal end of the sheath. A pair of wings are bonded to the proximal end of the sheath to faciliate separation. The hub connector and sheath are bonded by a web extending axially from a shoulder of the hub connector and including a pair of web tabs arranged on radially opposite sides of the hub connector. The web tabs are bonded to the sheath across respective separation lines, thereby preventing premature separation of the peelable sheath portions. The web also includes a pair of web support struts, arranged on radially opposite sides of the hub and rotated about 90° relative to the web tabs, that are bonded to the respective wings to prevent premature separation of the hub connector from the sheath.

14 Claims, 4 Drawing Sheets

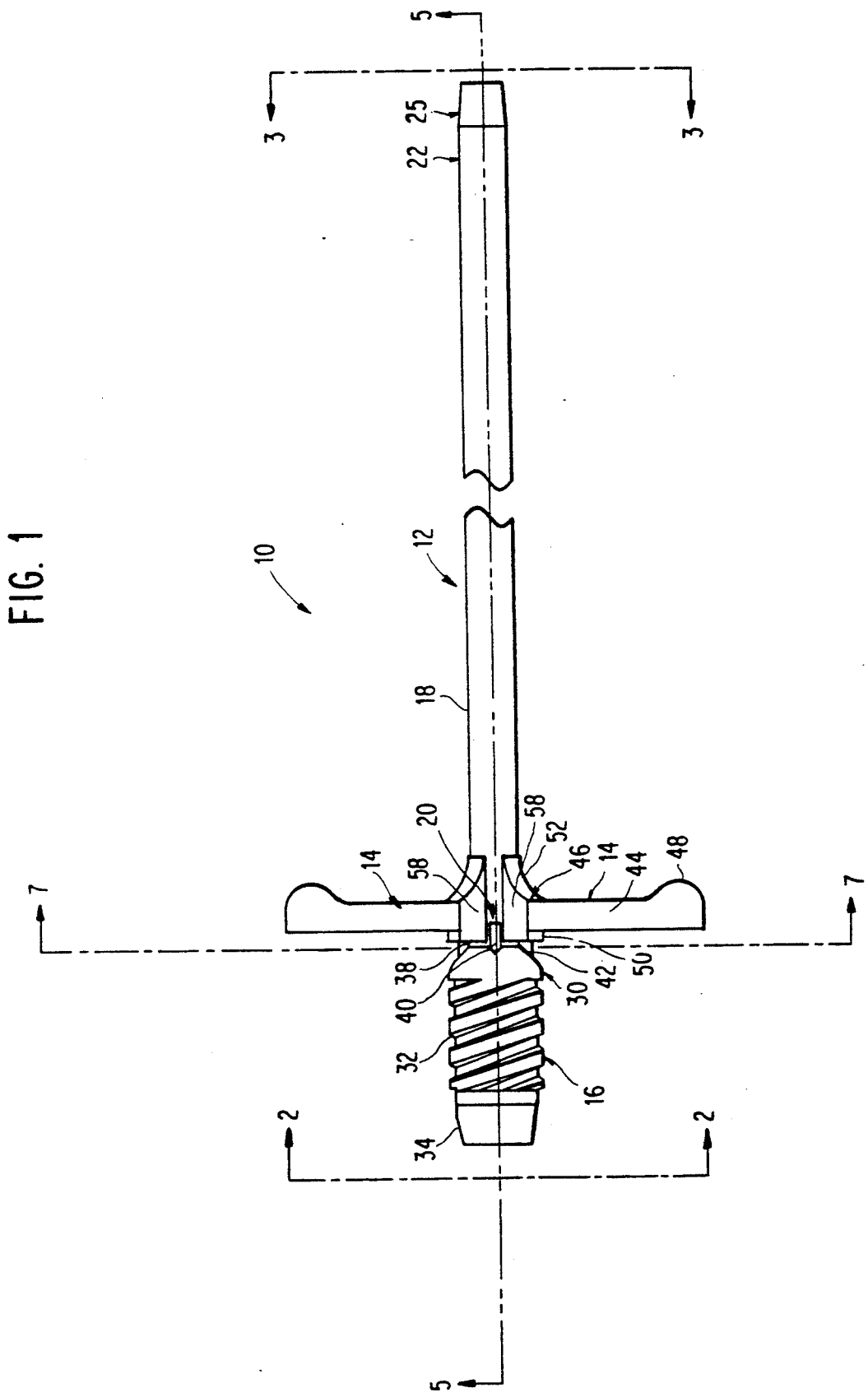

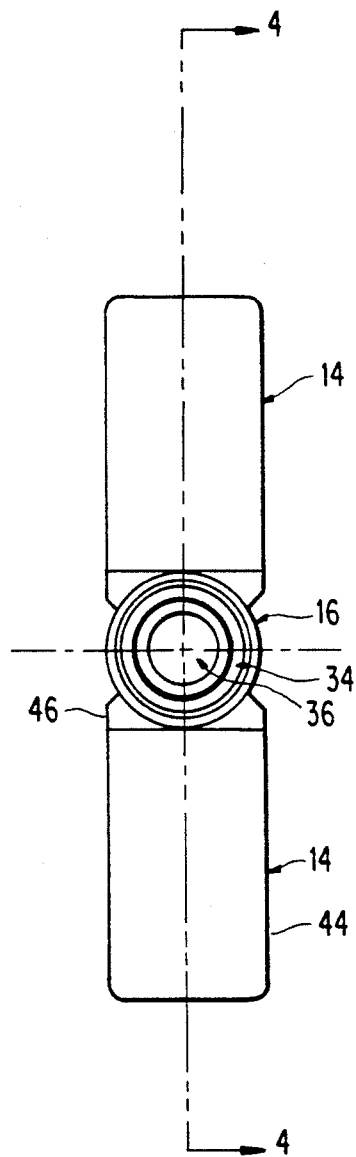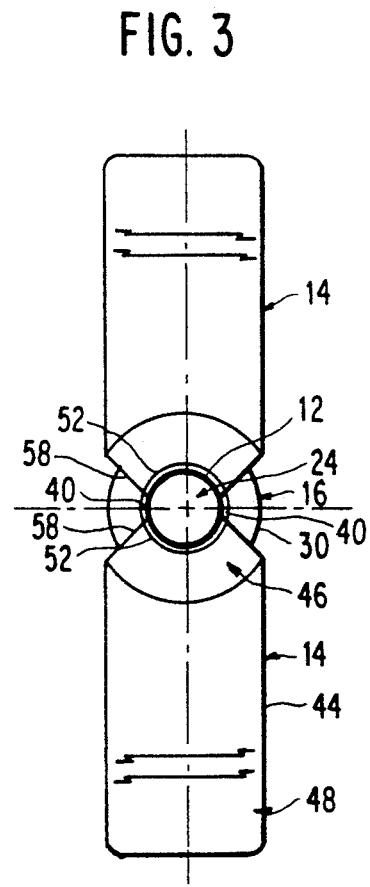

PEELABLE SHEATH WITH HUB CONNECTOR

BACKGROUND OF THE INVENTION

1. Field of the Invention

The present invention relates generally to medical devices and procedures that use catheters, or similar devices. More particularly, the present invention relates to a peelable sheath having a hub connector useable with such catheters or other devices. The invention has particular utility in percutaneous medical procedures. However, the present invention also may be found to have utility in other medical procedures or applications.

2. Description of the Prior Art

Sheaths for medical procedures are well known, particularly in percutaneous medical procedures. Generally, percutaneous medical devices, such as catheters, guide wires, or the like, are introduced into a body channel, such as a vein or artery, e.g. the femoral artery, through a sheath.

A sheath generally includes a slender, flexible tube arranged for insertion into the body channel to maintain an opening which allows communication with such channel. After insertion of the sheath, but before insertion of a catheter, it may be desirable to introduce fluids, such as a heparin flush, into the body channel. Therefore, it is desirable to provide structure for attaching the proximal end of the sheath to an external device, such as a pump or syringe.

It also may be desireable to provide structure for attaching the proximal end of the sheath to a dilator (e.g., to lock the sheath-dilator set together as one unit) or to the catheter passing through it (e.g., to prevent bleeding). In addition, it often is found to be advantageous, after the catheter has been fully inserted and manipulated into position, to remove the sheath, leaving only the catheter resident in the body channel. The present invention accommodates all these needs.

Of course, any device resident in a vein or artery reduces the volume of blood that can pass. Since a sheath is of larger diameter than the catheter passing through it, leaving the sheath resident in the vein or artery reduces the blood flow more than if only the smaller catheter is left resident therein. Accordingly, it may be desireable to remove the sheath and leave the catheter resident in the artery or vein. Unfortunately, conventional sheaths have a drawback in that typically they cannot be withdrawn after insertion of a catheter or other device. Most catheters terminate in enlarged hubs which prevent conventional sheaths from sliding off over the end. The sheath, therefore, must remain resident in the vein or artery throughout the procedure.

Peelable sheaths also are known. Generally, peelable sheaths permit removal of the sheath after insertion because it is not necessary for them to pass over the hub of the catheter. For example, U.S. Reissue Pat. No. No. 31,855 (Osborne) relates to a flexible cannula or sheath comprising material that readily tears in a longitudinal direction. The cannula is provided at its proximal end with a pair of open ended slits forming first and second tabs on opposite sides of the cannula. When the tabs are pulled apart, the cannula structure tears longitudinally along its length. Accordingly, the sheath can be removed by pulling the tabs apart after the catheter or other device has been inserted into the body.

U.S. Pat. Nos. 4,411,654 (Boarini) and 4,412,832 (Kling) each relate to a peelable introducer catheter or sheath also comprising a pair of open ended slits for facilitating tearing of the sheath along its longitudinal axis. Each of the Boarini and Kling patents further comprises a slidable sleeve, telescopically disposed at the proximal end of the sheath, for preventing premature tearing or disruption of the sheath, e.g. during insertion or manipulation.

U.S. Pat. No. 4,345,606 (Littleford) relates to a sleeve and introducer set in which the sleeve or sheath is partially split to facilitate removal. The introducer has a tapered end adapted to extend into a patient's body. The sleeve, formed of a hollow tube, has a first portion with an inner dimension greater than the outer dimension of the introducer and a second portion at the distal end of the sleeve which extends parallel to the introducer and in close engagement therewith. A gradual taper extends along the sleeve between the first and second portions. The sleeve has a longitudinal slit along the first portion, through the taper and terminating short of its forward extremity to permit the sleeve to be peeled away from, e.g., a pacemaker electrode after introduction. The slit, or severing means, comprises a plurality of "perforations" to form a weakened line along the length of the sleeve. Alternatively, the Littleford patent suggests the severing means may take the form of holes, through cuts, reduced wall thickness, or integral cutting agents, such as strings and the like.

In one embodiment of the Littleford patent, the introducer and sleeve also include corresponding hub and flange arrangements that provide a means for locking the two elements together, to prevent inadvertent motion of the sleeve with respect to the introducer as the two elements are being inserted into the patient. The sleeve includes a slit extending through the flange, along the first portion and through the taper, and terminating in the second portion.

Peelable sheaths provide advantages over prior sheaths. For example, as noted above, peelable sheaths can be withdrawn after insertion even if a catheter inserted therethrough has an enlarged hub. However, known peelable sheaths also have drawbacks. Peelable sheaths are more flexible than their predecessors and, thus, are not as responsive to manipulation, e.g., during insertion. This is particularly true for peelable sheaths having tabs preformed by open ended slits, such as described in the Boarini and Kling patents, because once the tabs are formed, the sheath loses much of its structural integrity.

The split sleeve introducer disclosed in the Littleford patent is an improvement over such prior sheaths in that it employs a flange structure. This flanged sheath generally is more responsive because the structural integrity of the sheath flange is more easily maintained until it is desired to peel away the sheath. The flange of the Littleford patent also provides an advantage in that the user can cap the flange with a finger or thumb, e.g., to reduce or prevent undesirable aspiration of the blood when the sheath is manipulated. However, since the slit extends through the flange of the Littleford device, it still is susceptible to premature splitting, e.g., by manipulation during insertion.

In addition, none of the split sheaths in these references are configured with a hub that is designed for attachment to an external device, such as a pump or syringe, as well as to a dilator or a catheter.

SUMMARY OF THE INVENTION

The present invention provides a peelable sheath having a hub arranged for attachment to an external device, such as a pump or syringe.

It also provides a peelable sheath having a hub designed for attachment to a catheter dilator or other device resident therein.

The peelable sheath of the present invention also has a hub that is configured to prevent premature splitting when manipulated, e.g., during insertion or when attached to an external device.

These and other features, attributes and advantages are achieved by the peelable sheath of the present invention, in which a hub connector, such as a luer lock fitting, is bonded to the proximal end of the peelable sheath. The hub connector may be molded to the sheath using a relatively thin, break-away web, and may be removed by bending or twisting. The peelable sheath further may include a pair of wings, also molded to the sheath at its proximal end, and arranged so that the sheath, after removal of the fitting, can be split simply by pulling the wings apart.

BRIEF DESCRIPTION OF THE DRAWINGS

A more complete appreciation of the present invention and the many attendant advantages thereof readily will be apparent with reference to the following detailed description of a preferred embodiment of the invention together with the accompanying drawings, wherein:

FIG. 1 is a plan view of a peelable sheath of the present invention.

FIG. 2 is a proximal end view of the peelable sheath depicted in FIG. 1.

FIG. 3 is a distal end view of the peelable sheath depicted in FIG. 1.

DETAILED DESCRIPTION OF THE PREFERRED EMBODIMENT

Figure 5:
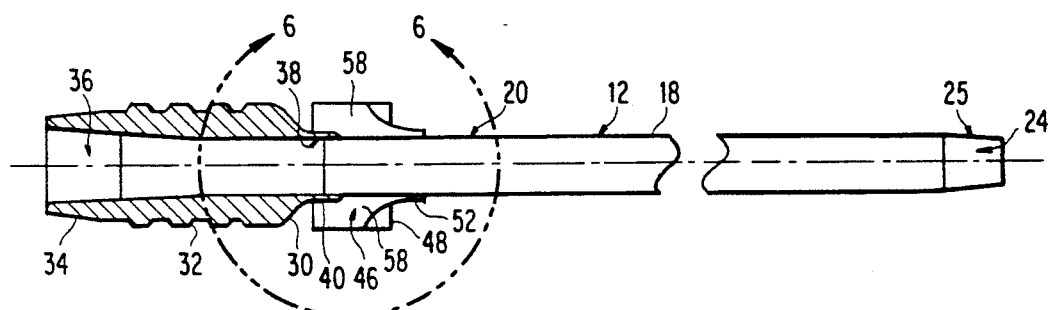
FIG. 5 is a cross-sectional view of the peelable sheath depicted in FIGS. 1 to 3, taken along lines 5—5 of FIG. 1, also illustrating its constituent parts.

Referring now to the drawings, wherein like reference numerals designate like or similar elements throughout, FIGS. 1 to 7 illustrate one embodiment of a peelable sheath of the present invention. The peelable sheath 10 generally comprises a sheath 12, a pair of wings 14 and a hub connector 16.

Sheath 12 generally comprises a flexible tube 18, having a cylindrical cross-section defining a lumen 24 therethrough, a proximal end 20, and a distal end 22. As in conventional peelable sheaths, the exterior side of distal end 22 includes a tapered portion 25 to facilitate insertion. Flexible tube 18 also includes separation lines 26 arranged longitudinally along the length of tube 18. In this embodiment, sheath 12 includes a pair of separation lines 26 arranged longitudinally on radially opposite sides of tube 18.

It will be appreciated that this arrangement of separation lines 26 forms a pair of peelable sheath portions 28, each being a semicylindrical shape and having a semicircular cross-section. As is well known in the art, separation means 26 may take many forms, including but not limited to perforations, score lines, slots and folds. Separation also can be accomplished by use of cutting devices such as integral strings, knife edges and the like. It will be appreciated that separation lines provide a structurally weakened line that will separate progressively along the line when peelable sheath portions 28 are pulled apart. Cutting devices can be employed to perform the same function. In the embodiment depicted in FIGS. 1 to 7, separation lines 26 are formed longitudinally in the inner wall of flexible tube 18. However, the form of separation lines 26 may vary depending on the particular application.

Figure 4:
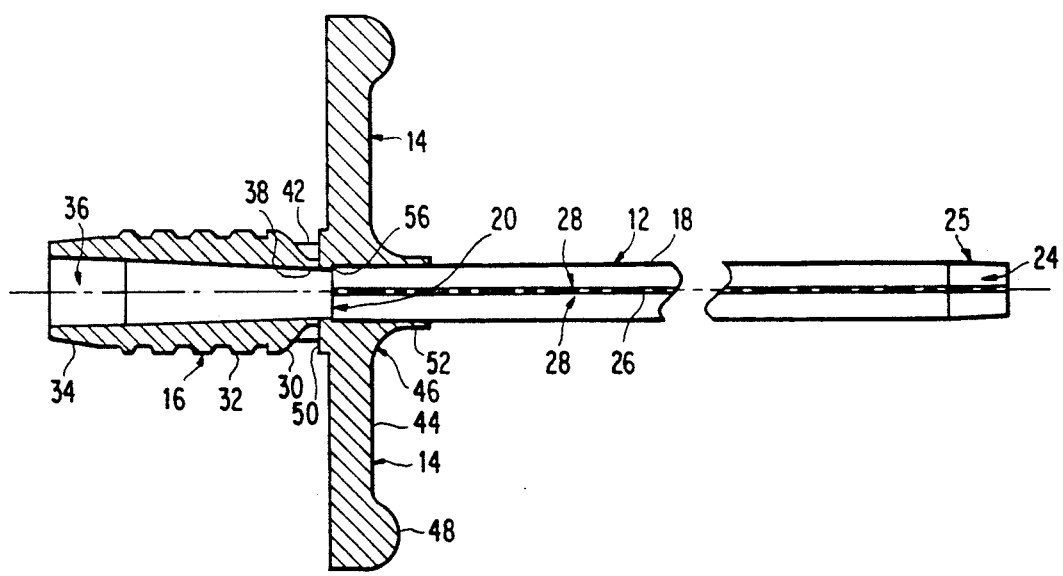
FIG. 4 is a cross-sectional view of the peelable sheath depicted in FIGS. 1 to 3, taken along lines 4—4 of FIG. 2, illustrating its constituent parts, including a flexible sheath, a pair of wing tabs and a hub connector.

Hub connector 16 can be attached to the proximal end 20 of tube 18 or to tabs 14. As best shown in FIGS. 1, 4 and 5, the hub connector 16 is a threaded luer lock fitting, which includes a shoulder portion 30, a threaded body portion 32 and a terminal end portion 34. Running through the entire length of connector 16 is hub lumen 36, having a generally cylindrical configuration, in fluid communication with sheath lumen 24 (see, e.g., FIGS. 4 and 5). Thus, it will be appreciated that peelable sheath 10 provides a continuous access lumen therethrough for insertion of secondary devices, such as catheters, or fluids. Of course, alternatives to the use of a thread on the luer lock will be readily apparent to those skilled in the art. For example, a tapered luer lock designed for a friction fit could be used, as could one made for a snap fit.

Figure 6:
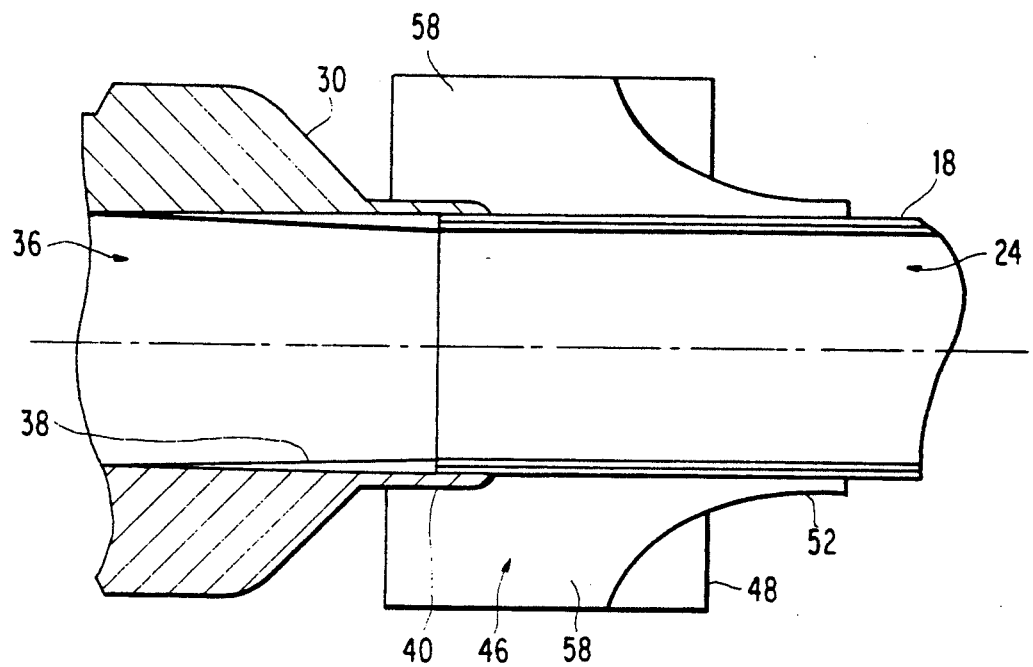
FIG. 6 is an enlarged longitudinal cross-sectional view of area 6—6 of FIG. 5, illustrating in detail an embodiment of a web bonding the hub connector to the wing tabs and peelable sheath portions of the peelable sheath depicted in FIGS. 1 to 3.
Figure 7:
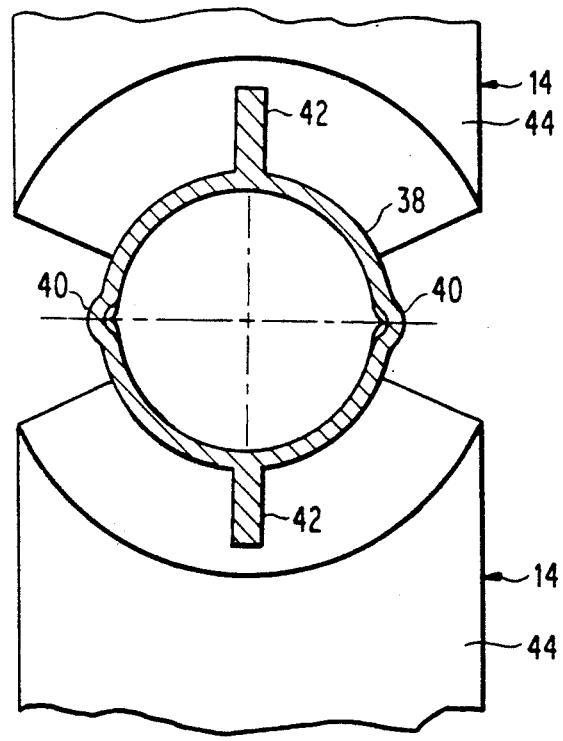
FIG. 7 is a cross-sectional view of a web connector of the present invention, taken along lines 7—7 of FIG. 1.

As best shown in FIGS. 5 and 6, hub connector 16 is bonded to proximal end 20 of tube 18 by web 38. More specifically, web 38 forms a thin annular neck or extension of shoulder portion 30. Web 38 may be bonded to tube 18 by injection or extrusion molding. However, those skilled in the art will appreciate that there are a wide variety of bonding methods which could be employed, the actual method chosen being dependent upon the nature of the materials, the particular application and personal preference.

Web 38 also has a pair of web tabs 40 and web support struts 42 (see, e.g., FIG. 1). Web tabs 40 extend from web 38 on radially opposite sides of hub connector 16. As discussed in greater detail below, web tabs 40 are bonded across separation lines 26 of sheath 12 to prevent premature splitting of separation lines 26. Web support struts 42 also are arranged on radially opposite sides of hub connector 16, and are radially offset from web tabs 40 by about 90°. As also is discussed in greater detail below, web support struts 42 are bonded to wings 14 to provide structural rigidity and to prevent premature separation from sheath 12.

Wings 14 also are bonded to sheath 12 at proximal end 20 of tube 18. A pair of wings 14 are bonded to respective peelable sheath portions 28. Each wing 14 includes a body portion 44, which extends radially from sheath 12, a foot portion 46, which is bonded to tube 18, and a rounded tip 48. Each foot portion further includes a semi-annular step 50, which forms a base for bonding web support strut 42 to wing 14, and a semi-annular throat portion 52, which tapers in the direction of distal end 22 of tube 18.

Referring again to FIGS. 2 to 3, each foot portion 46 forms a semicylindrically shaped base having an interior curve radius equal to the outer radius of tube 18. Each foot portion 46 also comprises a semicylindrical shaped detent 56 for receiving and abutting proximal end 20 of tube 18 (see FIG. 4). It will be appreciated that this arrangement provides both maximum surface interface and proper longitudinal registration of wings 14 relative to sheath 12. Finally, each foot portion 46 also has angled sides 58, that form a pair of wedge shaped channels between wings 14 on radially opposite sides of peelable sheath 10. As discussed in greater detail below, this arrangement and configuration provides respective longitudinal and radial points of leverage for facilitating initial separation of peelable sheath portions 28 by manipulating wings 14.

In the preferred embodiment, each of tube 18, hub connector 16 and wings 14 are composed of a biocompatible material suitable for use in medical procedures, e.g., a gamma-sterilizable plastic, preferably polyethylene. The material chosen also should facilitate manufacture using, e.g. extrusion or injection molding techniques. However, it will be appreciated that the materials and manufacturing methods may vary depending on the application and personal preferences.

In the embodiment depicted in FIGS. 1-7, hub connector 16 and wings 14 are one piece. Between shoulder 30 of connector 16 and wings 14, the material thickness is reduced so as to form a thin web 38.

In one method of use, peelable sheath 10 is inserted in a patient using conventional percutaneous medical procedures. That procedure would generally involve inserting the sheath of the present invention as part of a sheath-dilator set. After insertion of the sheath, the dilator or other introducer device typically would be withdrawn. To facilitate insertion, the sheath and dilator, or other introducer device, likely would be locked together using hub connector 16 (i.e., by connection to the threaded luer fitting). It will be appreciated that web tabs 40 and web support struts 42 provide additional structural integrity to peelable sheath 10 during insertion and manipulation of the peelable sheath and introducer device.

After insertion, the dilator then would normally be disconnected from hub connector 16 and withdrawn. A procedure device, such a pump or syringe, then could be connected to hub connector 16, e.g. to introduce fluids, such as a heparin flush, into the vein or artery or perhaps to draw blood. Alternatively, or following the use of the pump or syringe a catheter, such as a balloon catheter could be inserted through peelable sheath 10. The catheter also could be connected to hub connector 16 to prevent bleeding.

After insertion of a catheter, if it is determined that it is desirable to remove the sheath, that can be done simply by peeling the sheath apart. To do so, hub connector 16 first is bent or twisted relative to sheath 12, so that separation occurs at break-away web 38. Separating hub connector 16 also will tend to cause web tabs 40 to break-away from sheath 12 and web support struts 42 to break-away from wings 14.

To initiate separation of peelable sheath portions 28 along separation lines 26, wings 14 can be pinched together, e.g. by rotating them in opposite radial directions. It will be appreciated that, if not already separated by twisting, web tabs 40 and web support struts 42 then also will break-away from peelable sheath portions 28 and semi-annular steps 50, respectively, due to this manipulation. Sheath 12 then may be peeled away from the catheter by pulling wings 14 apart.

Numerous other embodiments, variations and modifications will be apparent to those skilled in the art and all such other embodiments, variations and modifications fall within the broad scope of the invention herein described and are intended to be covered thereby. It will be appreciated that the above description of one embodiment is illustrative only. It is not intended to limit the scope of the present invention, which is defined by the following claims.

What is claimed is:

1. A peelable sheath, comprising:
   a flexible tube having separation means for dividing said tube into a pair of peelable sheath portions;
   a hub attached to a proximal end of said tube, said hub being bonded to said tube by an annular web, and being separable from said tube by bending or twisting said hub relative to said sheath; and
   connecting means for connecting said tube to another device.

2. The peelable sheath of claim 1, further comprising a pair of wing members disposed at the proximal end of said tube and bonded, respectively, to said pair of peelable sheath portions, wherein said sheath portions can be peeled apart by pulling said wing members apart.

3. The peelable sheath of claim 2, wherein said hub also is bonded to said wing members.

4. The peelable sheath of claim 2, wherein said hub is connected to said sheath and wing members through said annular web.

5. The peelable sheath of claim 2, wherein said wing members are composed of polyethylene.

6. The sheath of claim 1, wherein said separation means are in a form selected from the group comprising fold lines, score lines, perforations, indentations, thinned wall portions, and integral cutting elements.

7. The sheath of claim 1, wherein said hub comprises a luer fitting.

8. The sheath of claim 7, wherein said luer fitting comprises a threaded body portion.

9. The peelable sheath of claim 1, wherein said flexible tube is composed of polyethylene.

10. The peelable sheath of claim 1, wherein said hub is composed of polyethylene.

11. The peelable sheath of claim 1, wherein said connecting means comprise a threaded fitting.

12. A peelable sheath, comprising:
    a flexible tube having separation means for dividing said tube into peelable sheath portions;
    a one-piece hub attached to a proximal end of said tube; and
    means for connecting said tube to another device.

13. A peelable sheath, comprising:
    a flexible tube having separation means for dividing said tube into peelable sheath portions;
    a fluid-tight hub attached to a proximal end of said tube; and
    means for connecting said tube to another device.

14. A peelable sheath, comprising:
    a flexible tube having separation means for dividing said tube into a plurality of peelable sheath portions;
    a hub attached to a proximal end of said tube, said hub being fluid tightly bonded to said tube, and separable from said tube by bending or twisting said hub relative to said sheath; and
    connecting means for connecting said tube to another device.

* * * * *